United States Patent
Pellegretti

(10) Patent No.: US 9,392,994 B2
(45) Date of Patent: Jul. 19, 2016

(54) APPARATUS AND METHOD FOR ULTRASOUND IMAGING WITH CONTRAST AGENTS

(75) Inventor: Paolo Pellegretti, Genoa (IT)

(73) Assignee: Esaote, S.p.A., Milan (IT)

( * ) Notice: Subject to any disclaimer, the term of this patent is extended or adjusted under 35 U.S.C. 154(b) by 959 days.

(21) Appl. No.: 13/439,053

(22) Filed: Apr. 4, 2012

(65) Prior Publication Data

US 2012/0259212 A1    Oct. 11, 2012

(30) Foreign Application Priority Data

Apr. 5, 2011 (IT) .............................. GE2011A0037

(51) Int. Cl.
*A61B 5/00* (2006.01)
*A61B 8/00* (2006.01)
*A61B 8/08* (2006.01)

(52) U.S. Cl.
CPC ............... *A61B 8/406* (2013.01); *A61B 8/0825* (2013.01); *A61B 8/481* (2013.01)

(58) Field of Classification Search
CPC .... A61B 5/4312; A61B 8/406; A61B 8/4209; A61B 8/4281; A61B 8/483; A61B 2019/5276
See application file for complete search history.

(56) References Cited

U.S. PATENT DOCUMENTS

| | | | |
|---|---|---|---|
| 6,514,206 B2 * | 2/2003 | Maxwell ................... | A61B 8/54 600/443 |
| 7,699,783 B2 | 4/2010 | Hanover et al. | |
| 7,771,360 B2 | 8/2010 | Johnson et al. | |
| 2004/0000841 A1 * | 1/2004 | Phelps et al. ................... | 310/314 |
| 2005/0143638 A1 * | 6/2005 | Johnson et al. ............... | 600/407 |
| 2008/0177180 A1 * | 7/2008 | Azhari et al. ................. | 600/439 |
| 2011/0201932 A1 * | 8/2011 | Duric et al. .................... | 600/443 |
| 2012/0109682 A1 * | 5/2012 | Seltzer et al. ...................... | 705/2 |

OTHER PUBLICATIONS

Ashfaq et al., A new approach towards ultrasonic transmission tomography with a standard ulrasound system, Ultrasonics Symposium, 2004 IEEE Montreal, Canada Aug. 23-27, 2004, Piscataway, NJ, IEEE vol. 3, Aug. 23, 2004, pp. 1848-1851.
Ermert et al., 2E-6 Contrast Enhaned Perfusion Imaging by means of Spatial Compounding, Ultrasonics Symposium 2006, IEEE PI, Oct. 1, 2006, pp. 424-427.
European Search Report from related case EP 12163037 dated Jul. 20, 2012.

(Continued)

*Primary Examiner* — Elmer Chao
(74) *Attorney, Agent, or Firm* — Woodard, Emhardt, Moriarty, McNett & Henry LLP

(57) ABSTRACT

Apparatus and method for detecting ultrasound images from a body under examination. The apparatus comprises a unit emitting ultrasound pulses and a unit receiving ultrasound pulses. The emitting unit and the receiving unit face each other and are spaced apart by a predetermined distance. These units are arranged at opposite sides of a cavity housing the body under examination. The ultrasound pulses emitted from the emitting unit are received by the receiving unit after passing through the body under examination and are transformed into transmission signals. Included is a control unit for the emitting unit, a unit processing the received signals, image generating device and image displaying device. The processing unit comprises a unit comparing the values of a propagation speed of ultrasound pulses and/or of the attenuation of ultrasound pulses with predetermined threshold values.

12 Claims, 6 Drawing Sheets

(56) References Cited

OTHER PUBLICATIONS

Italian Search report from related case IT GE20110037 dated Aug. 3, 2011.

Rizzatto et al., Importance of staging of breast cancer and role of contrast ultrasound, European Radiology, vol. 11, No. S3, Dec. 1, 2001, pp. E47-E52.

* cited by examiner

APPARATUS AND METHOD FOR ULTRASOUND IMAGING WITH CONTRAST AGENTS

CROSS-REFERENCE TO RELATED APPLICATION

This application claims the foreign priority benefit of Italian Application No. GE2011A000037, filed Apr. 5, 2011, the entire disclosure of which is hereby incorporated by reference.

BACKGROUND

The invention relates to an apparatus for detecting ultrasound images from a body under examination, which apparatus comprises a first unit emitting ultrasound pulses comprising one or more electroacoustic transducers and a first unit receiving ultrasound pulses comprising one or more electroacoustic transducers, said first emitting unit and said first receiving unit being faced each other and being spaced apart from each other by a predetermined distance such that they are arranged at opposite sides of a cavity housing said body under examination and the ultrasound pulses emitted from said first emitting unit are received by said first receiving unit after passing through the body under examination and are transformed into transmission signals, a control unit for said first emitting unit, a unit processing the received signals, image generating means and displaying means for said images, said processing unit comprising a unit evaluating the attenuation of ultrasound pulses and/or the propagation speed of ultrasound pulses.

The operation of such type of apparatuses is usually called as transmission mode, in which only the wave that has passed through the body is examined without considering the reflected echoes and by means of which it is possible to evaluate the propagation speed of ultrasound pulses when the ultrasound beam passes through the body under examination and the attenuation due to the structures of the body under examination.

It is also possible to use the transmission mode in combination with the reflection mode, by means of which it is possible to generate images by means of the echoes generated from the structures of the body under examination in response to the ultrasound beam transmitted to said body under examination.

Such technology can be used particularly in breast ultrasound imaging.

Apparatuses of this type are described in documents U.S. Pat. No. 7,699,783 and U.S. Pat. No. 7,771,360, which content is to be considered as a part of the present description.

In particular three types of images are produced by using the two different modes: images that represent maps of the propagation speed of ultrasound pulses and attenuation of ultrasound pulses of tissues for each point of the body under examination are generated by the transmission mode, while by the reflection mode tomographic images are generated.

Information about propagation speed of ultrasound pulses can be used for spatially correcting the geometric deformations in tomographic images due to tissues being heterogeneous.

As regards ultrasound imaging a widely used and increasingly developing method is the use of contrast agents, typically microbubbles that have a non-linear reflection behaviour and therefore that generate echoes with frequencies corresponding to fundamental frequency harmonics of the emission pulses transmitted to the body under examination.

The use of contrast agents is typically useful for investigating properties or conditions of blood flow and/or the condition of tissue vascularization.

There is a rising attention in using the so called "targeted" contrast agents, wherein microbubbles are associated to ligands that bind to receptors characteristic of specific diseases, causing contrast agents to gather in the areas affected by the disease.

In the known apparatuses described above there is the unsolved problem of recognizing the second harmonic signal components actually due to contrast agents, since the harmonic generation can be due to the non-linearity in scattering and propagation of ultrasounds in tissues.

This leads to the uncertainty in interpreting information obtained from imaging with contrast agents, while on the contrary the need of having reliable systems for recognizing the presence of contrast agents increases both in the analysis of blood flows according to the different modes and/or for several diagnostic purposes.

The present invention aims at solving the problems mentioned above by an apparatus as described hereinbefore and wherein in addition said processing unit comprises a unit comparing said values of propagation speed of ultrasound pulses and/or of the attenuation of ultrasound pulses with predetermined threshold values, the transmission signals resulting from the presence of contrast agents within the body under examination when the comparison of said attenuation of ultrasound pulses and/or of said propagation speed of ultrasound pulses has a specific difference with respect to the corresponding threshold value.

Depending on the type of contrast agent and of the tissue under examination, the values of the attenuation of ultrasound pulses or of the propagation speed of ultrasound pulses under the presence of contrast agents to be considered as indicating the presence of such contrast agents, can be under or over said threshold values.

Experimental studies have shown that, in the transmission ultrasound mode by means of which it is possible to obtain information about the propagation speed of ultrasound pulses and attenuation of ultrasound pulses, the presence of contrast agents can significantly affect the values of the propagation speed of ultrasound pulses and in particular of the attenuation of ultrasound pulses.

SUMMARY

The present invention has the advantage of exploiting this result for recognizing the presence in the body under examination of contrast agents and it reaches this only by simply comparing the attenuation of ultrasound pulses and/or the propagation speed of ultrasound pulses with predetermined threshold values.

In a further embodiment there is provided a second unit receiving ultrasound pulses, comprising one or more electroacoustic transducers, for receiving echoes generated by the body under examination and for transforming them into reflection signals, said processing unit comprising a unit for extracting harmonic distortion components of said reflection signals and said harmonic distortion components of the reflected signals resulting from a reflection due to contrast agents when the comparison of said attenuation of ultrasound pulses and/or of said propagation speed of ultrasound pulses in the reflection point from where the reflected pulse comes has a given difference with respect to the corresponding threshold value particularly the values of said attenuation of ultrasound pulses and/or of said propagation speed of ultrasound pulses can be under or over said threshold values depending on the cases.

The unit for extracting harmonic components can be anyone, such as for instance a digital or analog spectrography analysis unit, or in combination or as an alternative it can comprise digital or analog filters.

Thus the transmission mode can be combined with the reflection mode and moreover the so called harmonic imaging can be carried out such that the harmonic components of the reflected signal are selectively detected.

It is possible to provide, in combination or as an alternative, the use of harmonic components for the transmission mode such that one or more of the harmonic components of the transmitted signal is selectively detected.

According to a further embodiment there are provided a second emitting unit, comprising one or more electroacoustic transducers, and a control unit for said second emitting unit, such that the echoes received from the second receiving unit derive from the pulses emitted from said second emitting unit.

Thus for the transmission mode and the reflection mode respectively dedicated emitters and receivers are used, such that they can be carried out independently from each other.

In a further embodiment said second emitting unit and said second receiving unit comprise the same one or more electroacoustic transducers.

This allows only one transducer array dedicated to the reflection mode to be provided, as however it is provided in known ultrasound probes.

According to a further embodiment said second emitting unit and/or said second receiving unit are movable from a location near said first emitting unit to a location near said first receiving unit.

In a further embodiment said image generating means generate a transmission image from signals received by said first receiving unit and a reflection image from signals received by said second receiving unit, said unit evaluating the attenuation of ultrasound pulses and/or the propagation speed of ultrasound pulses of ultrasonic pulses calculates for each pixel or voxel of the transmission image the attenuation of ultrasound pulses and/or the propagation speed of ultrasound pulses, said unit extracting the harmonic components of said reflection signals calculates for each pixel or voxel of the reflection image the intensity of the harmonic components, said comparing unit compares for each corresponding pixel or voxel of the transmission image and of the reflection image the values of the attenuation of ultrasound pulses and/or of the propagation speed of ultrasound pulses and the intensity of the harmonic components with specific threshold values, thus detecting the presence of contrast agents for each pixel or voxel.

Thus the pixels or voxels corresponding to areas of the body under examination wherein the presence of contrast agents is detected are discriminated from those wherein it is not detected on the basis of the comparison of the harmonic components of the received signals in the reflection mode and of the values of attenuation of the ultrasound pulses obtained by the transmission mode.

Therefore this allows a spatial reference to be given to the presence of contrast agents in the body under examination and it allows three-dimensional diagrams of blood flows or perfusion maps to be reconstructed.

According to a further embodiment there are provided means for the suppression of the image contribution due to fundamental frequency signals of transmitted pulses such that only images deriving from signals of harmonic components are provided.

Such means are known and widely used in the several methods such as the so called pulse inversion or the like.

These means can be for example image subtraction means such that a first reflection image is acquired from harmonic components of reflection reception signals received by said second receiving unit with no contrast agents, then a second reflection image is acquired from harmonic components of reflection reception signals received by said second receiving unit with contrast agents, a subtraction is performed between said first reflection image and said second reflection image by said subtraction means, generating an image wherein for each pixel or voxel a determination is made whether the signal derives from the presence of a contrast agent by means of said comparing unit which compares for each pixel or voxel the intensity value of the harmonic components of the reflection reception signal and the value of the attenuation of ultrasound pulses and/or of the propagation speed of ultrasound pulses of the transmission reception signal acquired at the same time as said second reflection image with specific threshold values.

The subtraction of the first image acquired with no contrast agents from the second image acquired with contrast agents allows an image to be obtained wherein the most significant pixels and voxels mainly derive from contrast agents, but it will contain also information about reflectors into the body under examination that have a echogenic behaviour similar to that of the contrast agents.

In order to further distinguish which are the pixels actually related to the presence of contrast agents the resulting image is therefore analyzed in comparison with values of the propagation speed of ultrasound pulses and of attenuation of ultrasound pulses.

In a further embodiment said displaying means display said reflection image, highlighting in a different manner pixels or voxels wherein the presence of said contrast agents is detected.

Such displaying means can advantageously comprise a screen where the image is displayed with pixels or voxels wherein the presence of said contrast agents is detected coloured in a different manner than the remaining part of the image.

The injection of contrast agents is currently performed by dedicated devices, which are difficult to integrate with the apparatus performing the imaging.

To this end it is always necessary for the operators to control and adjust the administration of the contrast agent, with the consequent difficulty in obtaining processes that are automated and therefore more harmonized with the imaging process and more reliable.

According to a further embodiment there is provided a contrast agent injector comprising an injection needle, an inner tank intended to hold said contrast agents connected to said injection needle, means for releasing the injection of a specific dose of said contrast agents and means for moving said injection needle, said movement means and said injection releasing means being controllable by control means.

This guarantees the system administering the contrast agent to be integrated with the imaging system, for a better tendency in developing processes that are automated and therefore more harmonized with the imaging process and more reliable.

In a further embodiment said injector comprises reading means for a RFID apparatus associated to said inner tank holding said contrast agents and/or to an outer tank intended to fill said inner tank, which RFID apparatus has information about the type of contrast agent contained and about injection protocols relevant to that type of contrast agent stored therein.

This allows the process administering contrast agents to be automated relieving the user from the burden of completely managing all the administration steps.

In a further embodiment said movement means and said injection releasing means are controlled by said control means such that the injection protocol detected by said reading means is applied.

According to a further embodiment 3D images of the body under examination are generated.

According to a further embodiment the breast of a patient is subjected to imaging.

In a further embodiment there is provided a substantially horizontal table with the patient laying prone on it, said table being provided with at least a cavity housing the breast, said first emitting unit, said first receiving unit, said second emitting unit and said second receiving unit being housed within said cavity housing the breast, such that the breast is subjected to imaging in the uncompressed condition.

This leads to the advantage that it is possible to perform breast imaging with contrast agents in a normal perfusion condition, namely with the perfusion not affected by a compression of blood vessels from the outside.

The present invention further relates to an ultrasound imaging method for discriminating ultrasound signals deriving from contrast agents, which method comprises the following steps:

a) emitting an ultrasound beam at a fundamental frequency within said body under examination;

b) receiving said ultrasound beam transmitted by the body under examination obtaining transmission reception signals;

c) calculating the attenuation of ultrasound pulses and/or the propagation speed of transmitted ultrasound pulses by comparing the transmission reception signals with the corresponding emitted signals;

d) finding whether the transmission reception signal results from the presence of a contrast agent by comparing the values of the attenuation of ultrasound pulses and/or of the propagation speed of ultrasound pulses with specific threshold values.

By means of this method it is possible to discriminate the reception signals in which the presence of contrast agents is detected from those in which it is not detected on the basis of the comparison between the values of attenuation of the ultrasound pulses and/or of the propagation speed of ultrasound pulses obtained by the transmission mode, on the basis of the results from experimental studies mentioned above.

Such method does not provide the injection of contrast agents as a step.

In a further embodiment the method of the present invention comprises the following further steps:

e) receiving echoes generated by the reflection of said transmitted ultrasound beam obtaining reflection reception signals;

f) extracting harmonic components from said reflection reception signals;

g) finding whether said harmonic components of the reflection reception signals are due to a reflection by contrast agents by comparing the intensity values of the harmonic components and/or said attenuation of ultrasound pulses and/or said propagation speed of ultrasound pulses with specific threshold values.

In a further embodiment before step e) a second ultrasound beam at a fundamental frequency is emitted into said body under examination such that the echoes received for obtaining the reflection reception signals derive from said second emitted ultrasound beam.

In a further embodiment the method of the present invention comprises the following further steps:

g) generating a transmission image from said transmission reception signals;

h) generating a reflection image from harmonic components of said reflection reception signals;

i) possibly registering the transmission image and the reflection image with the same reference system;

j) calculating for each pixel or voxel of the transmission image the attenuation of ultrasound pulses and/or the propagation speed of ultrasound pulses of the transmission reception signal;

k) calculating for each pixel or voxel of the reflection image the intensity of the harmonic components of the reflection reception signal;

l) finding out whether for each pixel or voxel the signal results from the presence of the contrast agent or from a general resonator or reflector by comparing for each pixel or voxel the value of the attenuation of ultrasound pulses and/or of the propagation speed of ultrasound pulses of the transmission reception signal and the intensity value of the harmonic components of the reflection reception signal with specific threshold values.

According to a further embodiment a first reflection image is acquired from harmonic components of reflection reception signals with no contrast agents, then a second reflection image is acquired from harmonic components of reflection reception signals with contrast agents, a subtraction is performed between said first reflection image and said second reflection image, generating an image wherein for each pixel or voxel a determination is made whether the signal results from the presence of a contrast agent by comparing for each pixel or voxel the intensity value of the harmonic components of the reflection reception signal and the value of the attenuation of ultrasound pulses and/or of the propagation speed of ultrasound pulses of the transmission reception signal acquired at the same time as said second reflection image with specific threshold values.

In a further embodiment transmission images and reflection images are 3D images obtained by sequentially scanning planes parallel each other of said body under examination.

According to a further embodiment the breast is subjected to imaging in an uncompressed condition.

The present invention further relates to a method for controlling an apparatus for detecting ultrasound images from a body under examination, which apparatus comprises a first unit emitting ultrasound pulses comprising one or more electroacoustic transducers and a first unit receiving ultrasound pulses comprising one or more electroacoustic transducers, said first emitting unit and said first receiving unit being faced each other and being spaced apart from each other by a predetermined distance such that they are arranged at opposite sides of a cavity housing said body under examination and the ultrasound pulses emitted from said first emitting unit are received by said first receiving unit after passing through the body under examination and are transformed into transmission signals, a second unit receiving ultrasound pulses, comprising one or more electroacoustic transducers, for receiving echoes generated by the body under examination and for transforming them into reflection signals, a control unit for said first emitting unit, a unit processing the received signals, image generating means and displaying means for said images, said processing unit comprising a unit evaluating the attenuation of ultrasound pulses and/or the propagation speed of ultrasound pulses and a unit extracting the harmonic components of said reflection signals, wherein said processing unit comprises a unit comparing said values of the intensity of said harmonic components, of the propagation speed of ultrasound pulses and/or of the attenuation of ultrasound pulses with specific threshold values, transmission and reflection signals resulting from the presence of contrast agents within the body under examination when the comparison of said harmonic components of the reflected signals, of said attenuation of ultrasound pulses and/or of said propagation speed of ultrasound pulses is under or over said threshold values.

These and other characteristics and advantages of the present invention will be more clear from the following description of some embodiments shown in annexed drawings.

DESCRIPTION OF THE SELECTED EMBODIMENTS

Figure 1:
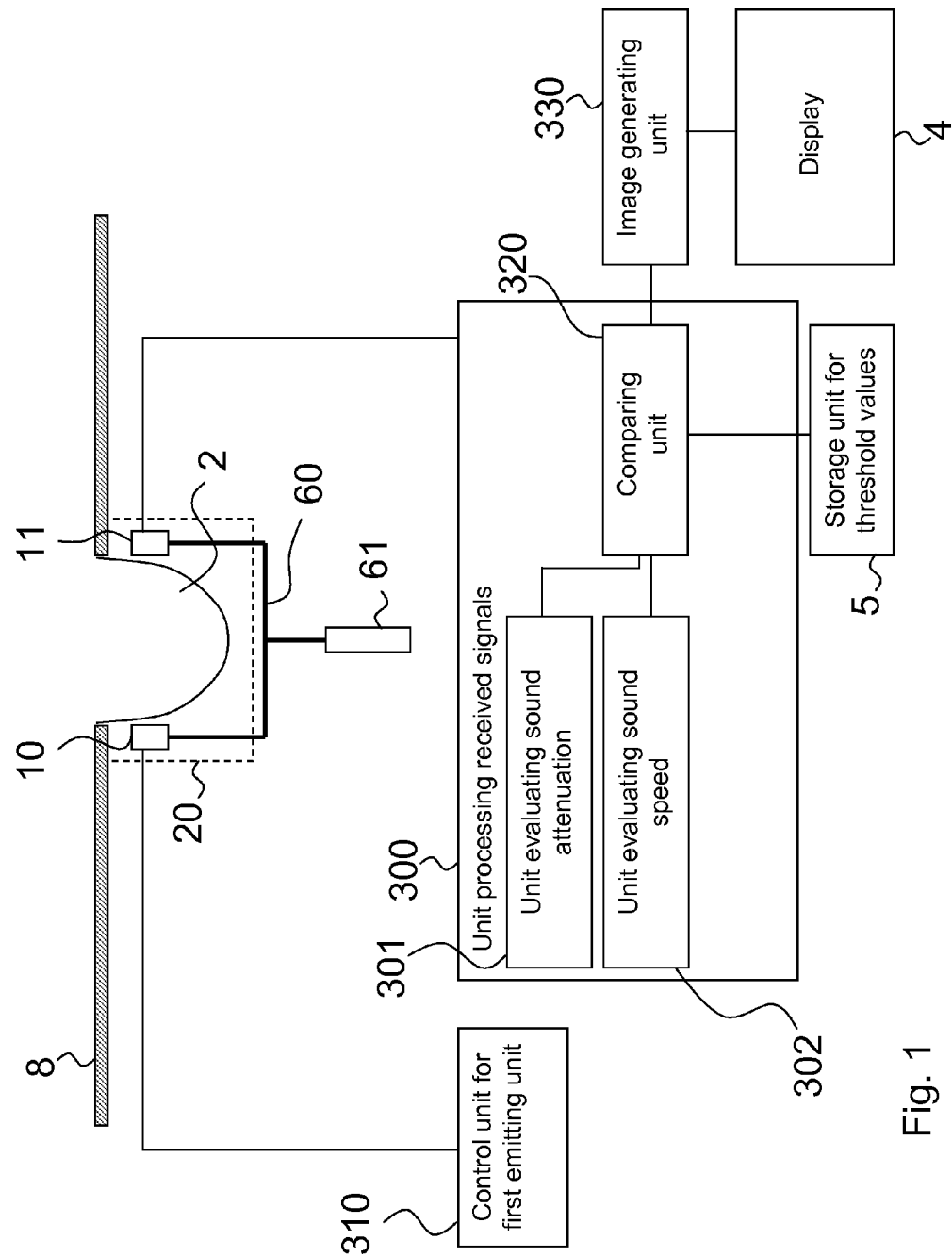
FIG. 1 is a diagrammatic illustration of one embodiment of the apparatus of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIG. 1 shows a preferred embodiment of the apparatus of the present invention.

The apparatus described is of the type according to documents U.S. Pat. No. 7,699,783 and U.S. Pat. No. 7,771,360 and it has a substantially horizontal table 8 with a patient laying prone on it, which table is provided with a cavity 20 housing the breast 2, where the breast 2 is housed suspended and not in the compressed condition.

Within the housing cavity there are provided a first unit 10 emitting ultrasound pulses comprising one or more electroacoustic transducers and a first unit 11 receiving ultrasound pulses comprising one or more electroacoustic transducers.

The first emitting unit 10 and the first receiving unit 11 are faced each other and are spaced apart from each other by a predetermined distance such that they are arranged at opposite sides of the cavity 20 housing the breast 2.

The ultrasound pulses emitted from the first emitting unit 10 are received by the first receiving unit 11 after passing through the breast 2 and are transformed into transmission signals.

The apparatus further comprises a control unit 320 for the first emitting unit, a unit 300 processing the received signals, an image generating unit 330 and image displaying means, particularly a display 4.

The processing unit 300 further comprises a unit evaluating the attenuation of ultrasound pulses 301 and/or the propagation speed of ultrasound pulses 302.

The processing unit comprises a unit 320 comparing the values of the propagation speed of ultrasound pulses and/or of the attenuation of ultrasound pulses calculated by the unit evaluating the attenuation of ultrasound pulses 301 and by the unit evaluating the propagation speed of ultrasound pulses 302 respectively, where they are compared with predetermined threshold values, stored into a storage unit 5 for the threshold values.

The transmission signals therefore result from the presence of contrast agents within the body under examination when the comparison of the values of attenuation of ultrasound pulses and/or of the propagation speed of ultrasound pulses is under or over the threshold values stored into the storage unit 5 for the threshold values.

Therefore an image is generated by the image generating unit 330 and it is displayed on the display 4 and pixels or voxels of the image in which the presence of said contrast agents is detected are displayed in a different colour than the remaining part of the image.

The first emitting unit 10 and the first receiving unit 11 are supported by a support element 60, which is moved by an actuator 61 such to rotate on itself about a vertical axis substantially passing by the centre of the housing cavity 20 and such to translate from a lowermost position to an uppermost position.

Thus 3D images are generated by sequentially scanning planes parallel to each other of said body under examination.

Figure 5:
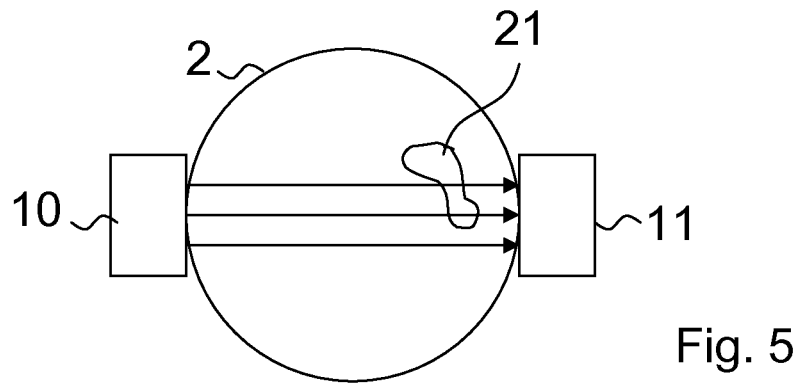
FIG. 5 is a diagrammatic illustration of one embodiment of an emitting-receiving apparatus according to the present invention.

This arrangement corresponds to what shown in FIG. 5, wherein the first emitting unit 10 and the first receiving unit 11 are shown, faced each other on opposed side of the breast 2 under examination.

A part of the ultrasound pulses emitted from the first emitting unit 10 are received by the first receiving unit 11 after passing through an area 21 of the breast 2 where contrast agents are provided, undergoing the consequent changes in the attenuation of the ultrasound pulses and propagation speed of ultrasound pulses.

Therefore this arrangement allows a method comprising the following step to be carried out:

a) emitting an ultrasound beam at a fundamental frequency within said body under examination;

b) receiving said ultrasound beam transmitted by the body under examination obtaining transmission reception signals;

c) calculating the attenuation of ultrasound pulses and/or the propagation speed of transmitted ultrasound pulses by comparing the transmission reception signals with the corresponding emitted signals;

d) finding whether the transmission reception signal results from the presence of a contrast agent by comparing the values of the attenuation of ultrasound pulses and/or of the propagation speed of ultrasound pulses with specific threshold values.

Such method does not provide the injection of contrast agents as a step.

Figure 2:
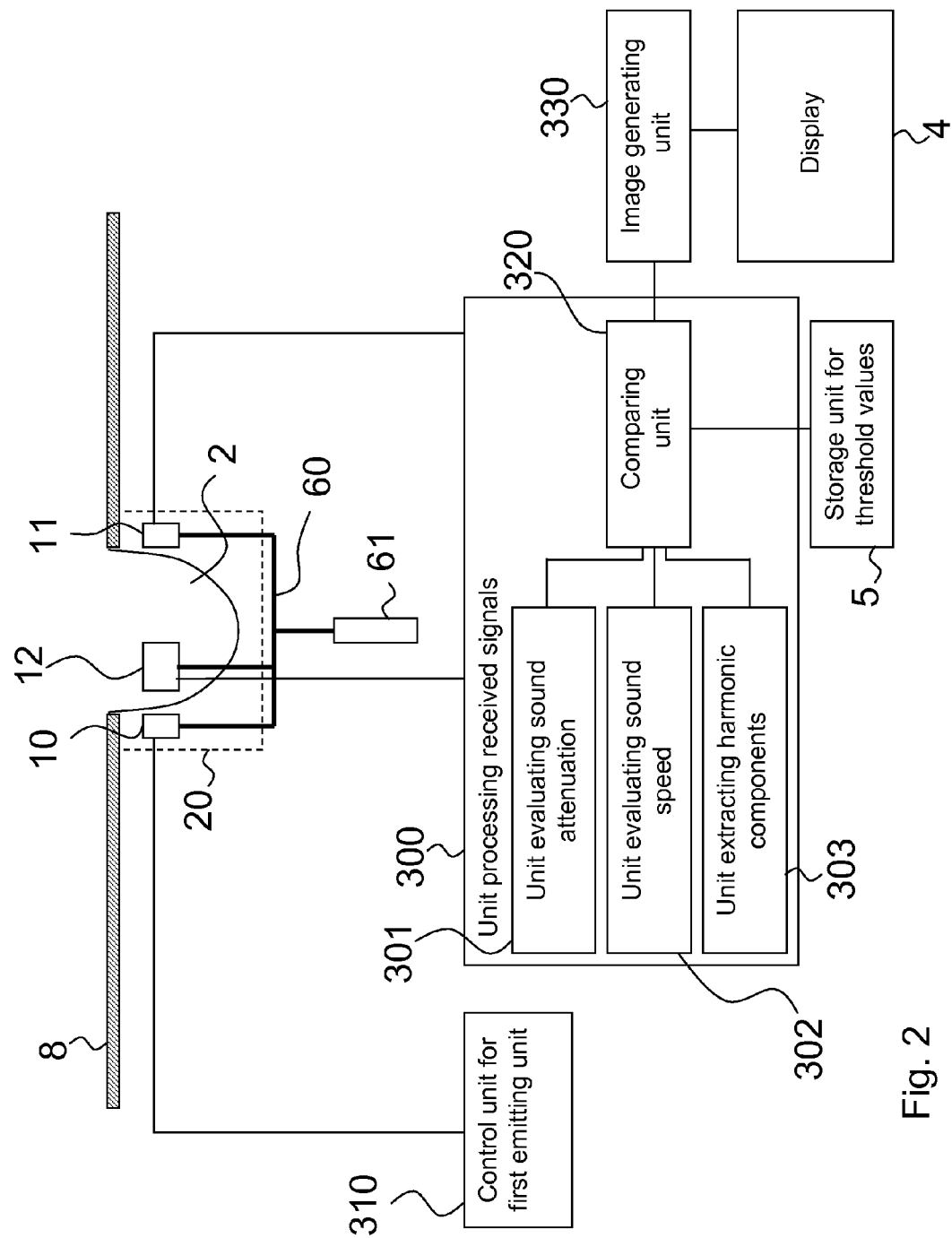
FIG. 2 is a diagrammatic illustration of another embodiment of the apparatus of the present invention.

In the embodiment shown in FIG. 2 there is further provided a second receiving unit 12 for ultrasound pulses, comprising one or more electroacoustic transducers, for receiving echoes generated by the body under examination and for transforming them into reflection signals.

The processing unit further comprises a unit 303 for extracting harmonic components of the reflection signals.

The harmonic components of the reflected signals extracted in this manner therefore result from a reflection due to contrast agents when the comparison of said attenuation of ultrasound pulses and/or of said propagation speed of ultrasound pulses is under or over the threshold values stored into the storage unit 5 for the threshold values.

Figure 6:
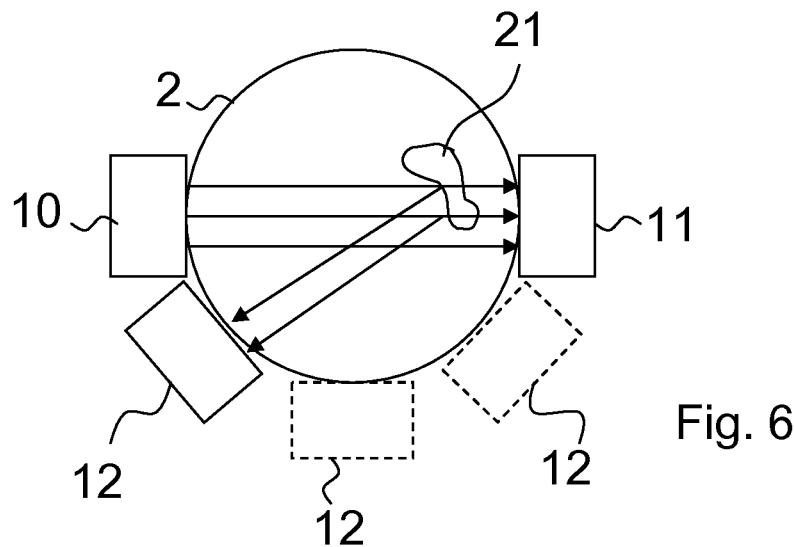
FIG. 6 is a diagrammatic illustration of another embodiment of an emitting-receiving apparatus according to the present invention.

This arrangement corresponds to what shown in FIG. 6, wherein the second receiving unit 12 is shown, which can be moved in different positions, some of them are shown by broken lines, from a position near the first emitting unit 10 to a position near the first receiving unit 11.

A part of the ultrasound pulses emitted from the first emitting unit 10 are partially reflected by an area 21 of the breast 2 where contrast agents are provided, and the corresponding echoes, comprising harmonic components due to the non-linear behaviour of the contrast agents, are received by the second receiving unit 12.

This arrangement allows a method comprising the following further steps to be carried out:

e) receiving echoes generated by the reflection of said transmitted ultrasound beam obtaining reflection reception signals;

f) extracting harmonic components from said reflection reception signals;

g) finding whether said harmonic components of the reflection reception signals are due to a reflection by contrast agents by comparing the intensity value of the harmonic components and/or said attenuation of ultrasound pulses and/or said propagation speed of ultrasound pulses with specific threshold values.

Figure 3:
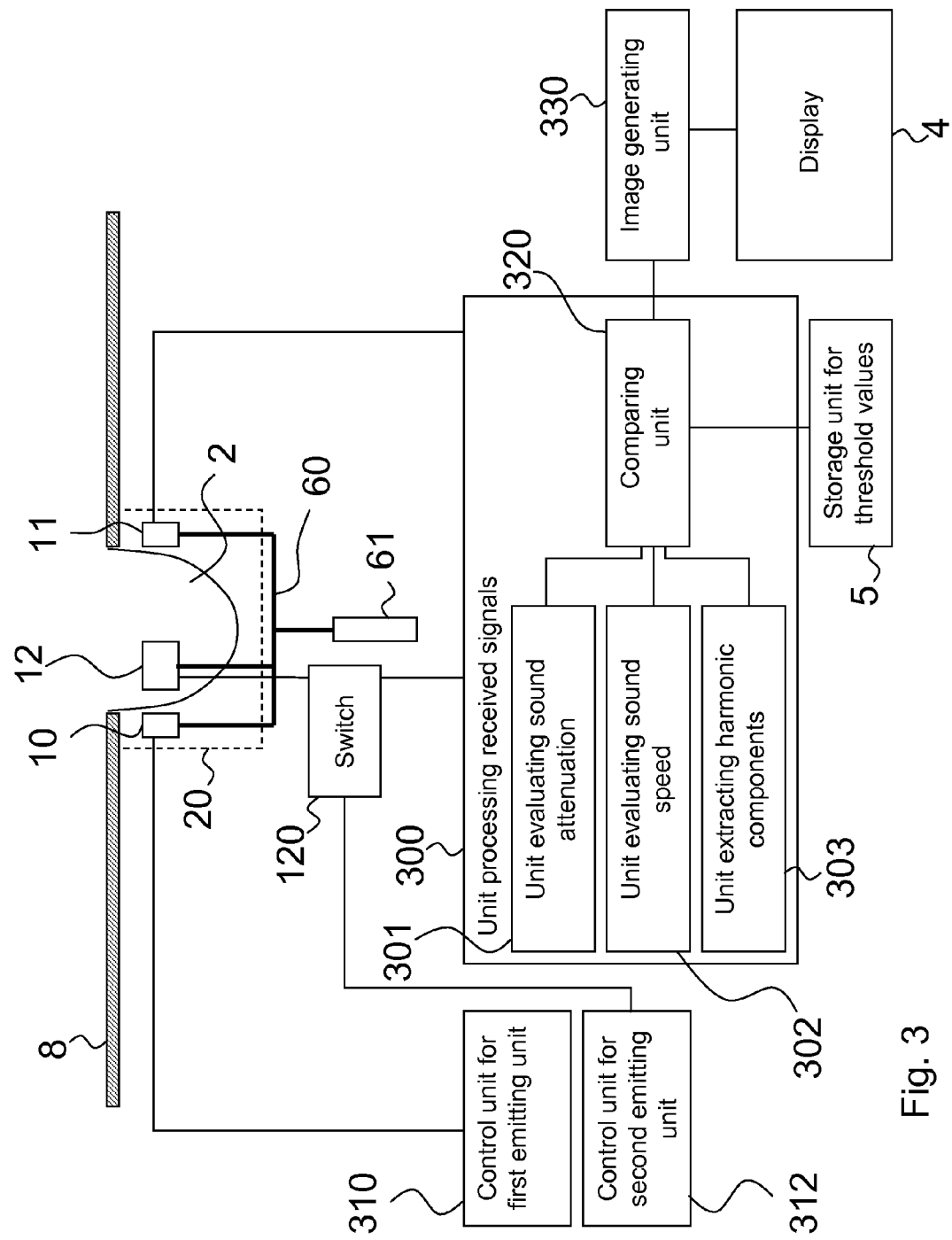
FIG. 3 is a diagrammatic illustration of another embodiment of the apparatus of the present invention.

In a further embodiment shown in FIG. 3 there is provided a second emitting unit, comprising one or more electroacoustic transducers, denoted in figure with number 12 since it comprises the same one or more electroacoustic transducers of the second receiving unit 12.

There is further provided a control unit 312 for said second emitting unit and the echoes received by the second receiving unit 12 derive from pulses emitted from the second emitting unit 12.

A switch 120 is provided among the control unit 312 for the second emitting unit, the processing unit 300 for the received signals and the second emitting and receiving unit 12, such that it is possible to alternately send signals to the electroacoustic transducers and to receive signals therefrom.

The image generating unit 330 generates a transmission image from signals received by the first receiving unit 11 and a reflection image from signals received from the second receiving unit 12.

The unit evaluating the attenuation of ultrasound pulses 302 and the unit evaluating the propagation speed of ultrasound pulses 301 calculate for each voxel of the transmission image the attenuation of ultrasound pulses and the propagation speed of ultrasound pulses.

The unit 303 extracting the harmonic components of the reflection signals extracts the harmonic components of the reflection signals and it calculates for each voxel of the reflection image the intensity of the harmonic components.

The comparing unit 320 compares for each corresponding voxel of the transmission image and of the reflection image the values of the attenuation of ultrasound pulses and of the propagation speed of ultrasound pulses and the intensity of the harmonic components with specific threshold values stored into the storage unit 5 for the threshold values, by detecting for each voxel the presence of contrast agents.

Figure 7:
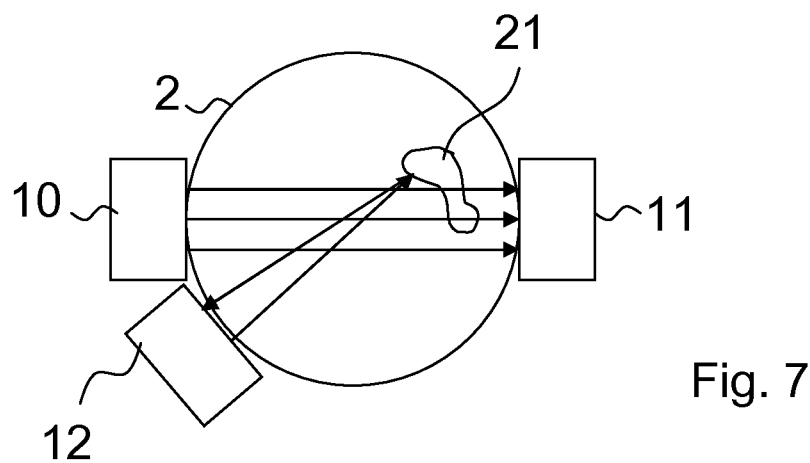
FIG. 7 is a diagrammatic illustration of another embodiment of an emitting-receiving apparatus according to the present invention.

The arrangement shown in FIG. 3 corresponds to what shown in FIG. 7, wherein the second receiving unit 12 and the second emitting unit 12 coincide, such that the same electroacoustic transducers emit the ultrasound pulses and receive the corresponding echoes.

This arrangement allows a method as described above to be carried out, wherein before step e) a second ultrasound beam is emitted into said body under examination at a fundamental frequency such that the echoes received for obtaining the reflection reception signals derive from said second ultrasound beam emitted.

Moreover it is possible to carry out a method comprising the following further steps:

g) generating a transmission image from said transmission reception signals;

h) generating a reflection image from harmonic components of said reflection reception signals;

i) possibly registering the transmission image and the reflection image with the same reference system;

j) calculating for each pixel or voxel of the transmission image the attenuation of ultrasound pulses and/or the propagation speed of ultrasound pulses of the transmission reception signal;

k) calculating for each pixel or voxel of the reflection image the intensity of the harmonic components of the reflection reception signal;

l) finding out whether for each pixel or voxel the signal results from the presence of the contrast agent or from a general resonator or reflector by comparing for each pixel or voxel the value of the attenuation of ultrasound pulses and/or of the propagation speed of ultrasound pulses of the transmission reception signal and the intensity value of the harmonic components of the reflection reception signal with specific threshold values.

Figure 4:
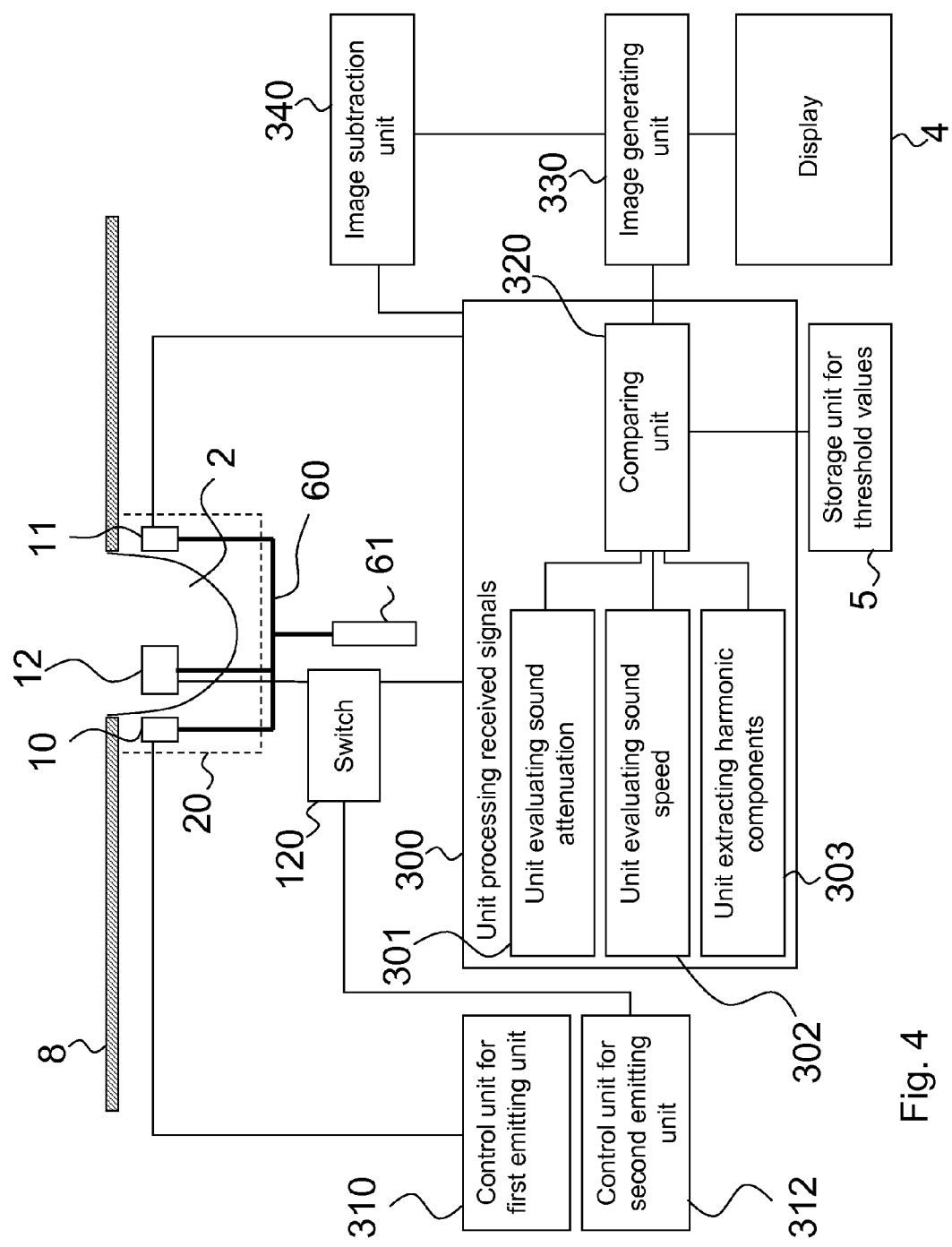
FIG. 4 is a diagrammatic illustration of another embodiment of the apparatus of the present invention.

In a further embodiment shown in FIG. 4 there is provided an image subtraction unit 340.

A first reflection image is acquired from harmonic components of reflection reception signals received by said second receiving unit with no contrast agents, then a second reflection image is acquired from harmonic components of reflection reception signals received by said second receiving unit with contrast agents, and the image subtraction unit 340 makes a subtraction between the first reflection image and the second reflection image.

Thus an image is generated wherein for each pixel or voxel a determination is made whether the signal results from the presence of a contrast agent said comparing unit comparing for each pixel or voxel the intensity value of the harmonic components of the reflection reception signal and the value of the attenuation of ultrasound pulses and/or of the propagation speed of ultrasound pulses of the transmission reception signal acquired at the same time as said second reflection image with specific threshold values.

This arrangement allows a method to be carried out wherein a first reflection image is acquired from harmonic components of reflection reception signals with no contrast agents, then a second reflection image is acquired from harmonic components of reflection reception signals with contrast agents, a subtraction is performed between said first reflection image and said second reflection image, generating an image wherein for each pixel or voxel a determination is made whether the signal results from the presence of a contrast agent by comparing for each pixel or voxel the intensity value of the harmonic components of the reflection reception signal and the value of the attenuation of ultrasound pulses and/or of the propagation speed of ultrasound pulses of the transmission reception signal acquired at the same time as said second reflection image with specific threshold values.

Figure 8:
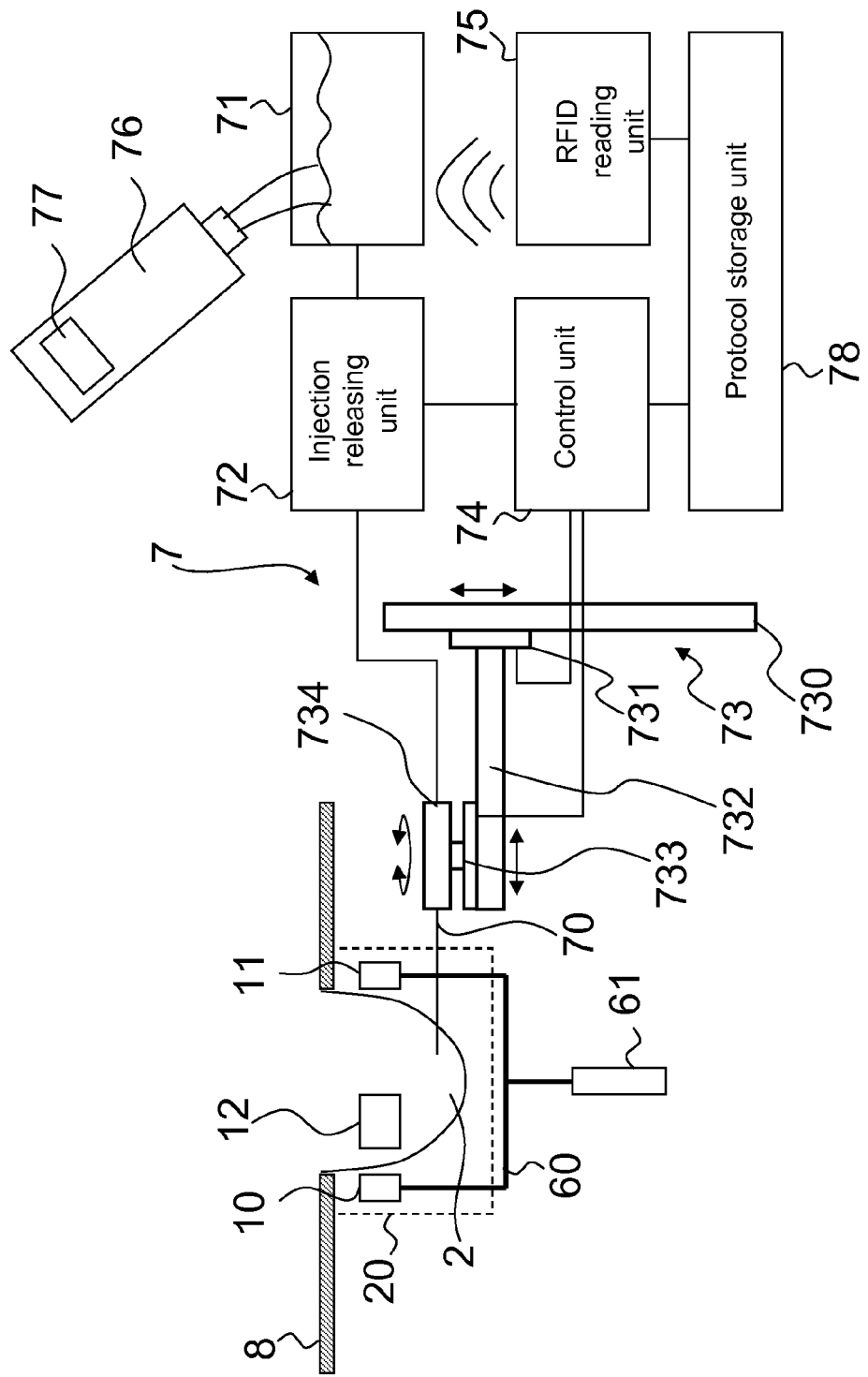
FIG. 8 is an embodiment of the part injecting contrast agents of the apparatus of the present invention.

FIG. 8 shows a further embodiment wherein there is provided a contrast agent injector 7 comprising an injection needle 70, an inner tank 71 intended to hold the contrast agents connected to said injection needle 70, a unit 72 for releasing the injection of a specific dose of the contrast agents and means 73 for moving the injection needle 70, the movement means 73 and the injection releasing unit 72 being controllable by a control unit 74.

The movement means 73 shown in the figure are composed of a mechanical arm comprising a vertical upright 730, upon which a vertical slide 731 is mounted which is translatable for at least a part of the vertical upright 730, as shown by the corresponding arrow.

To the vertical slide 731 there is pivotably coupled a horizontal arm 732, upon which a horizontal slide 733 is mounted which is translatable for at least a part of the horizontal arm 732, as shown by the corresponding arrow.

To the horizontal slide 733 there is coupled a support element 734 for the injection needle 70, which is rotatable about an axis perpendicular to the injection needle, as shown by the corresponding arrow.

The vertical slide 731, the horizontal slide 733 and the support element 734 are motorized and controllable by the control unit 74.

The movement means 73 as an alternative can be composed of mechanical arms of any type or the like.

The injector 7 comprises a reading unit 75 for a RFID apparatus 77 associated to an outer tank 76 intended to fill the inner tank 71.

The RFID apparatus 77 has information about the type of contrast agent contained and about injection protocols relevant to that type of contrast agent stored therein.

In a further embodiment the RFID apparatus 77 is associated to the inner tank 71 intended to hold said contrast agents, the inner tank being removable and replaceable.

A protocol storage unit 78 is provided wherein the injection protocols detected by the RFID reading unit 75 are stored.

The movement means 73 and the injection releasing unit 72 are controlled by the control unit 74 such that the injection protocol detected by the RFID reading unit 75 and stored within the protocol storage unit 78 is applied.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An apparatus for generating ultrasound images of a body part under examination, the apparatus comprising:
    a first ultrasound emitting unit comprising one or more electroacoustic transducers and a first ultrasound receiving unit comprising one or more electroacoustic transducers, said first ultrasound emitting unit and said first ultrasound receiving unit facing each other and being spaced apart from each other by a predetermined distance such that they are arranged at opposite sides of a cavity for housing the body part under examination, wherein ultrasound pulses emitted from said first ultrasound emitting unit are received by said first ultrasound receiving unit after passing through the body part under examination and are transformed into transmission signals;
    a control unit for controlling said first ultrasound emitting unit, a processing unit for processing the received signals from said first ultrasound receiving unit, an image generator, and a display for displaying images from said image generator;
    wherein said processing unit comprises an evaluating unit that evaluates the attenuation of ultrasound pulses and/or the propagation speed of ultrasound pulses;
    wherein said processing unit comprises a comparing unit that compares values of the propagation speed of ultrasound pulses and/or of the attenuation of ultrasound pulses with predetermined threshold values, wherein attenuation and/or propagation speed values under or over said predetermined threshold values indicate the presence of contrast agents within the body part under examination; and
    a second ultrasound receiving unit for receiving ultrasound pulses, comprising one or more electroacoustic transducers, for receiving echoes generated by the body part under examination and for transforming them into reflection signals, said processing unit comprising a extracting unit for extracting harmonic components of said reflection signals and said harmonic components of the reflected signals resulting from a reflection due to contrast agents when the comparison of said attenuation of ultrasound pulses and/or of said propagation speed of ultrasound pulses is under or over said threshold values;
    wherein said image generator generates a transmission image from signals received by said first ultrasound receiving unit and a reflection image from signals received by said second ultrasound receiving unit, wherein said evaluating unit evaluates the attenuation of ultrasound pulses and/or the propagation speed of ultrasound pulses by calculating for each pixel or voxel of the transmission image the attenuation of ultrasound pulses and/or the propagation speed of ultrasound pulses, wherein said extracting unit extracts the harmonic components of the reflection signals and calculates for each pixel or voxel of the reflection image the intensity of the harmonic components, wherein said comparing unit compares for each corresponding pixel or voxel of the transmission image and of the reflection image the values of the attenuation of ultrasound pulses and/or of the propagation speed of ultrasound pulses and the intensity of the second harmonic component with specific threshold values so as to detect the presence of contrast agents for each pixel or voxel.

2. The apparatus according to claim 1, comprising a second emitting unit having one or more electroacoustic transducers, and a control unit for said second emitting unit, wherein echoes received by the second ultrasound receiving unit result from pulses emitted from said second emitting unit.

3. The apparatus according to claim 2, wherein said second emitting unit and said second ultrasound receiving unit comprise the same one or more electroacoustic transducers.

4. The apparatus according to claim 2, wherein said second emitting unit and/or said second ultrasound receiving unit are movable from a location near said first ultrasound emitting unit to a location near said first ultrasound receiving unit.

5. The apparatus according to claim 1, comprising an image subtraction unit such that a first reflection image is acquired from harmonic components of reflection reception signals received by said second ultrasound receiving unit with no contrast agents, then a second reflection image is acquired from harmonic components of reflection reception signals received by said second ultrasound receiving unit with contrast agents, a subtraction is performed between said first reflection image and said second reflection image by said subtraction unit, generating an image wherein for each pixel or voxel a determination is made whether the signal results from the presence of a contrast agent by means of said comparing unit which compares for each pixel or voxel the intensity value of the harmonic components of the reflection reception signal and the value of the attenuation of ultrasound pulses and/or of the propagation speed of ultrasound pulses of the transmission reception signal acquired at the same time as said second reflection image with specific threshold values.

6. The apparatus according to claim 1, wherein said display displays said reflection image, highlighting in a manner pixels or voxels wherein the presence of said contrast agents is detected.

7. The apparatus according claim 1, comprising a contrast agent injector including an injection needle, an inner tank intended to hold said contrast agents connected to said injection needle, an injection releasing unit for releasing the injection of a specific dose of said contrast agents and a movement member for moving said injection needle, said movement member and said injection releasing unit being controllable by a controller.

8. The apparatus according to claim 7, wherein said injector comprises a reading unit for reading an RFID apparatus associated to said inner tank holding said contrast agents and/or to an outer tank intended to fill said inner tank, which RFID apparatus has information about the type of contrast agent and about injection protocols relevant to that type of contrast agent stored therein.

9. The apparatus according to claim 8, wherein said controller controls said movement member and said injection releasing unit so that the injection protocol detected by said reading unit can be applied.

10. A method comprising using the apparatus according to claim 1 to generate 3D images of the body part under examination.

11. A method comprising using the apparatus according to claim 1 to generate ultrasound images of a breast of a patient.

12. The apparatus of claim 2, comprising a substantially horizontal table, said table defining said cavity for housing the body part under examination, said first ultrasound emitting unit, said first ultrasound receiving unit, said second emitting unit and said second ultrasound receiving unit being housed within said cavity, such that the body part under examination can be subjected to imaging in an uncompressed condition.

* * * * *